US006846846B2

(12) United States Patent
Modak et al.

(10) Patent No.: US 6,846,846 B2
(45) Date of Patent: Jan. 25, 2005

(54) GENTLE-ACTING SKIN DISINFECTANTS

(75) Inventors: Shanta Modak, Riveredge, NJ (US); Trupti A. Gaonkar, New York, NY (US); Lester Sampath, Nyack, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 141 days.

(21) Appl. No.: 10/047,631

(22) Filed: Oct. 23, 2001

(65) Prior Publication Data

US 2003/0152644 A1 Aug. 14, 2003

(51) Int. Cl.⁷ ............... A61K 31/08; A61K 31/14; A61K 31/27; A61K 07/32

(52) U.S. Cl. ............... 514/722; 514/642; 514/643; 514/491; 514/494; 514/635; 424/65

(58) Field of Search ............... 514/494, 635, 514/643, 722, 642, 481; 424/65

(56) References Cited

U.S. PATENT DOCUMENTS

| | | | |
|---|---|---|---|
| 4,243,657 A | 1/1981 | Okumura et al. | 424/47 |
| 4,919,837 A | 4/1990 | Gluck | 252/106 |
| 4,956,170 A | 9/1990 | Lee | 424/81 |
| 5,516,510 A | 5/1996 | Beilfuss et al. | 424/65 |
| 5,591,442 A | 1/1997 | Diehl et al. | 424/401 |
| 5,705,532 A | 1/1998 | Modak et al. | 514/635 |
| 5,736,574 A | 4/1998 | Burnier et al. | 514/568 |
| 5,763,412 A | 6/1998 | Khan et al. | 514/23 |
| 5,776,430 A | 7/1998 | Osborne et al. | 424/43 |
| 5,830,488 A | 11/1998 | Suzuki et al. | 424/405 |
| 5,885,562 A | 3/1999 | Lowry et al. | 424/65 |
| 5,965,610 A | 10/1999 | Modak et al. | 514/494 |
| 5,980,477 A | 11/1999 | Kelly | 602/77 |
| 5,985,918 A * | 11/1999 | Modak et al. | 514/494 |
| 5,985,931 A | 11/1999 | Modak et al. | 514/634 |
| 5,989,531 A | 11/1999 | Schamper et al. | 424/65 |
| 6,022,551 A * | 2/2000 | Jampani et al. | 424/405 |
| 6,037,386 A | 3/2000 | Modak et al. | |
| 6,040,347 A | 3/2000 | Cupferman et al. | 514/723 |
| 6,045,817 A | 4/2000 | Ananthapadmanabhan et al. | 424/405 |
| 6,107,261 A | 8/2000 | Taylor et al. | 510/131 |
| 6,136,771 A | 10/2000 | Taylor et al. | 510/388 |
| 6,187,327 B1 | 2/2001 | Stack | 424/405 |
| 6,204,230 B1 | 3/2001 | Taylor et al. | 510/131 |
| 6,211,243 B1 | 4/2001 | Johnson | 514/634 |
| 6,323,171 B1 | 11/2001 | Fonsny et al. | 510/384 |
| 6,387,357 B1 | 5/2002 | Chopra et al. | 424/65 |
| 6,414,032 B1 | 7/2002 | Johnson | 514/634 |
| 6,420,431 B1 | 7/2002 | Johnson | 514/634 |
| 6,426,062 B1 | 7/2002 | Chopra et al. | 424/65 |
| 6,613,312 B2 * | 9/2003 | Rizvi et al. | 424/65 |
| 2002/0022660 A1 | 2/2002 | Jampani et al. | |

FOREIGN PATENT DOCUMENTS

| | | |
|---|---|---|
| DE | 4140474 | 6/1993 |
| DE | 4240674 | 3/1994 |
| EP | 0313302 | 4/1989 |
| EP | 0604848 | 7/1994 |
| FR | 2729050 | 7/1996 |
| WO | 0037042 | 6/2000 |

OTHER PUBLICATIONS

"Parfums, Cosmetiques, Aromes: Japan approves sale of new cosmetics ingredient," Chemical Business Newsbase, Jan. 16, 2001.

"A–Z of exhibitors; at Central European Coatings Show," PPCJ. Polymers Paint Colour Journal, No. 4433, vol. 190, p. 42, Oct. 1, 2000.

Woodruff, J. "Mixed feelings," Soap Perfumery & Cosmetics, No. 9, vol. 73, p. 39, Sep. 1, 2000.

"Happi, Household & Personal Products Industry: New ingredients galore at SCC supplier's day," Chemical Business Newsbase, Aug. 1, 2000.

"Manufacturing Chemist: Japan approve Schulke & Mayr's Sensiva SC 50," Chemical Business Newsbase, Jul. 14, 2000.

"S & M in Japan—Schulke & Mayr's Sensiva SC 50 deodorant active ingredient received approva for use in the Japanese market," SPC Asia No. 21, p. 35, May 2000.

"SPC, Soap Perfumery and Cosmetics: New for deodorants: Sensiva SC 50," Chemical Business Newsbase, Aug. 12, 1999.

Beilfuss, "A multifunctional ingredient for deodorants," SOFW Journal, 1998, vol. 124, p. 360, 362–364, 366.

"Fraicher de Peau Fresh Skin Body Mist," International Product Alert, No. 9, vol. 14, May 5, 1997.

(List continued on next page.)

Primary Examiner—Theodore J. Criares
(74) Attorney, Agent, or Firm—Baker Botts L.L.P.

(57) ABSTRACT

Antimicrobial compositions having synergistic combinations of octoxyglycerin and at least one other antimicrobial agent in formulations which are more effective than prior art compositions without causing increased irritation to the skin of the average user. In certain embodiments, skin irritation may be minimized by low concentrations of antimicrobials and/or the presence of soothing compounds such as zinc. Preferred embodiments include combinations of octoxyglycerin, a quaternary compound, and at least one other antimicrobial agent. Without being bound to any particular theory, it is hypothesized that the unexpected antimicrobial effectiveness of combinations of octoxyglycerin may result from an enhancement of the permeability of microbes to antimicrobials caused by octoxyglycerin.

40 Claims, No Drawings

OTHER PUBLICATIONS

"Schwarzkopf: Moving into a new area," European Cosmetic Markets, No. 9, Sep. 1, 1996.

Robinson, K. "Heat beating technology; deodorant market," Soap Perfumery and Cosmetics, v. 69 No. 7 p. 34, Jul. 1996.

"Vichy launches oil–free moisturizer," Chemist & Druggist, p. 792, Jun. 8, 1996.

"Schwarzkopf cares," European Cosmetic Markets, No. 5, vol. 13, May 1, 1996.

Sensiva® SC 50 product description from manufacturer website (www.schuelke–mayr.com), Schülke & Mayr, manufacturer, printed Apr. 4, 2001.

Sensiva® SC 50 now also approved in Japan, *Noderstedt*, Aug. 2000, Archived news report from Manufacturer website(www.shuelke–mayr.com), Schülke & Mayr, manufacturer, printed Apr. 4, 2001.

* cited by examiner

GENTLE-ACTING SKIN DISINFECTANTS

1. INTRODUCTION

The present invention provides for skin-friendly antimicrobial compositions comprising synergistic combinations of octoxyglycerin and a low concentration of an antibiotic, particularly chlorhexidine. In particular embodiments, the compositions further comprise a quaternary ammonium compound that enhances killing of microbes.

2. BACKGROUND OF THE INVENTION

"Skin disinfectants" are routinely used in professional and non-professional contexts to rapidly kill microbes. A physician has a need to disinfect his or her skin both before and after examining a patient. Prior to the performance of an invasive medical procedure, the skin of the subject must be properly cleaned to avoid post-procedure infections. In non-professional contexts, a commuter, riding public transportation, may wish to disinfect her hands before handling food; a child, playing in a park, may need to clean his hands but not have the convenience of soap and water nearby. Each of these situations require, optimally, a skin disinfectant that is effective, easy to use, and non-irritating so as to permit repeated use.

A number of skin disinfectants have been developed that use alcohol as the primary antimicrobial agent. There are two general problems associated with alcohol-based disinfectants. First, the effective concentration of alcohol, generally regarded to be greater than about 60 percent weight (hereafter, all percentages should be considered weight/ volume percentages, unless specified otherwise) of ethanol, or its equivalent, is irritating to the skin, causing dryness and consequent peeling and cracking. Because chapped skin tends to be more susceptible to microbial contamination, repeated use of alcohol disinfectants can exacerbate the very problem they are intended to solve. Second, whereas alcohol can be an effective disinfectant, once it evaporates its antimicrobial activity is lost.

Alcohol-based skin disinfectants which are known in the art, some of which address the two problems mentioned above, include the following.

U.S. Pat. No. 6,107,261 by Taylor et al., issued Aug. 22, 2000, and its continuations-in-part, U.S. Pat. No. 6,204,230 by Taylor et al., issued Mar. 20, 2001 and U.S. Pat. No. 6,136,771 by Taylor et al., issued Oct. 24, 2000, disclose antibacterial compositions which contain an antibacterial agent at a percent saturation of at least 50 percent. The compositions further comprise, as solubility promoters, a surfactant and a hydric solvent, which may be an alcohol.

U.S. Pat. No. 5,776,430 by Osborne et al., issued Jul. 7, 1998, discloses a topical antimicrobial cleaner containing about 0.65–0.85 percent chlorhexidine and about 50–60 percent denatured alcohol, which is scrubbed onto and then rinsed off the skin.

European Patent Application 0604 848 discloses a gel comprising an antimicrobial agent, 40–90 percent by weight of an alcohol, and a polymer and thickening agent.

U.S. Pat. No. 4,956,170 by Lee, issued Sep. 11, 1990 relates to a high alcohol content antimicrobial gel composition which comprises various emollients and a humectant to protect the skin from the drying effects of the alcohol. In alcohol formulations, higher levels of alcohol are needed to provide instant kill against sensitive as well as resistant strains of bacteria.

Certain formulations virtually omit alcohol as a primary antimicrobial agent, such as, for example, the skin sanitizing compositions disclosed in U.S. Pat. No. 6,187,327 by Stack, issued Feb. 13, 2001, which comprises triclosan (2,4,4'-trichloro-2'-hydroxydiphenyl ether; concentration 0.1–0.35 weight percent) in a topical lotion comprised of a surfactant phase and a wax phase, which purportedly provides antimicrobial protection for 3–4 hours after application. The composition prepared according to the claims of U.S. Pat. No. 6,187,327 further comprises chlorhexidine digluconate.

U.S. Pat. No. 5,965,610 by Modak et al., issued Oct. 12, 1999, teaches skin cleaning compositions comprising antimicrobial agents and zinc salts, where zinc salts have a soothing effect on the skin. The claimed subject matter includes formulations comprising a gel formed between zinc gluconate, chlorhexidine gluconate and a solvent, to which various thickening agents, emulsifying agents and/or emollients may be added.

U.S. Pat. No. 5,985,918 by Modak et al., issued Nov. 16, 1999, relates to "Zinc-Based Anti-Irritant Creams".

U.S. Pat. No. 5,705,532 by Modak et al., issued Jan. 6, 1998, relates to "Triple Antimicrobial Compositions" comprising less than or equal to two percent of a chlorhexidine compound, less than or equal to 0.1 percent of a quaternary ammonium compound, and less than or equal to two percent parachlorometaxylenol.

Octoxyglycerin, sold under the trade name Sensiva® SC50 (Schulke & Mayr), is a glycerol alkyl ether known to be gentle to the skin. Octoxyglycerine exhibits antimicrobial activity against a variety of Gram-positive bacteria associated with perspiration odor, such as *Micrococcus luteus, Corynebacterium aquaticum, Corynebacterium flavescens, Corynebacterium callunae*, and *Corynebacterium nephredi*, and is used in various skin deodorant preparations at concentrations between about 0.2 and 3 percent (Sensiva® product literature, Schulke & Mayr).

For example, U.S. Pat. No. 5,885,562 by Lowry et al., issued Mar. 23, 1999, relates to deodorant compositions comprising an antimicrobial agent, namely polyhexamethylene biguanide (at a concentration of between 0.01 and 0.5 percent), together with a polarity modifier such as Sensiva®SC50, at levels of typically 1–15 percent. Compositions disclosed in U.S. Pat. No. 5,885,562 may further comprise a short chain monohydric alcohol such as ethanol at a level of between 20 and 80 percent. Formulations useful as deodorants, however, would differ from those used as skin sanitizers in that skin sanitizers would optimally exhibit rapid broad spectrum activity against bacteria, fungi, and viruses, not merely gram positive odor causing bacteria.

U.S. Pat. No. 5,516,510 by Beilfuss et al., issued May 14, 1996, discloses deodorant compositions which comprise glycerin monoalkyl ethers such as octoxyglycerin (referred to therein as 2-ethyl hexyl glycerin ether, and as being the most preferred among these compounds). The deodorant compositions of U.S. Pat. No. 5,516,510 may be formulated in aqueous and/or alcoholic solutions and may further comprise additional antimicrobial compounds, including triclosan, chlorhexidine salts, alexidine salts, and phenoxyethanol, among others. Specific concentration ranges for triclosan and the biguanides are not provided.

3. SUMMARY OF THE INVENTION

The present invention relates to antimicrobial compositions comprising synergistic combinations of octoxyglycerin and at least one other antimicrobial agent in formulations which are more effective than prior art compositions without causing increased irritation to the skin of the average user. In certain embodiments, skin irritation may be minimized by low concentrations of antimicrobials and/or the presence of soothing compounds such as zinc. Preferred embodiments of the invention comprise combinations of octoxyglycerin, a quaternary ammonium compound, and at least one other antimicrobial agent. Without being bound to any particular theory, it is hypothesized that the unexpected antimicrobial effectiveness of combinations of octoxyglycerin may result from an enhancement of the permeability of microbes to antimicrobials caused by octoxyglycerin.

4. DETAILED DESCRIPTION OF THE INVENTION

The present invention relates to combinations of octoxyglycerin with at least one, and preferably at least two, antimicrobial agents. In preferred embodiments of the invention such compositions comprise octoxyglycerin and a quaternary ammonium compound.

Octoxyglyerin, as used herein, is also known as glycerol 1-(2-ethylhexyl) ether and is sold under the trade name Sensiva® SC 50 ("Sensiva®") by Schulke & Mayr (Rockaway, N.J.). Octoxyglycerin has the following chemical structure:

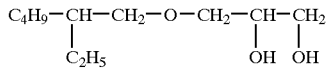

which has the empirical formula $C_{11}H_{24}O_3$. The CAS No. of octoxyglycerin is 70445-33-9. Octoxyglycerin has a relative molecular weight of 204.31 g/mol. Sensiva® SC 50 is sold as a clear, almost colorless liquid, having a refractive index of approximately 1.451, a density at 20° C. of approximately 0.95 g/ml, a boiling point of >285° C., a flash point of 152° C., a water solubility at 22° C. of approximately 1.8 g/l and virtually complete solubility in fat. In addition to having antimicrobial activity, it acts as a mild humectant and skin emollient. The present invention provides for compositions comprising octoxyglycerin at between 1 and 5 percent, and preferably 1–3 percent. It should be noted that all ranges recited herein are inclusive of their limiting values. Sensiva SC50 is essentially pure octoxyglycerin.

Antimicrobial agents which may be used in addition to octoxyglycerin according to the invention include biguanides and phenols. Biguanides may be used in concentrations between about 0.05 and 4 percent and preferably between about 0.05 and 2 percent. Examples of suitable biguanides include polyhexamethylene biguanide (PHMB) at concentrations between about 0.3 and 1 percent, alexidine at concentrations between about 0.5 and 2 percent, and chlorhexidine compounds at concentrations between about 0.5 and 4 percent and preferably between about 0.05 and 1 percent. A chlorhexidine compound, as that term is used herein, includes chlorhexidine free base as well as chlorhexidine salts, including, but not limited to, chlorhexidine diacetate (also known as "chlorhexidine acetate"), chlorhexidine digluconate (also known as "chlorhexidine gluconate"), chlorhexidine palmitate, chlorhexidine diphosphanilate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-alpha-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. Most preferably, the chlorhexidine compound is chlorhexidine digluconate a concentration between 0.05 and 4 percent.

Phenols (phenol derivatives) which may be used according to the invention include, but are not limited to, 2-hydroxyphenol compounds such as triclosan (2,4,4'-trichloro-2'-hydroxydiphenyl ether, also available as IRGASAN DP300 from Ciba Specialty Chemicals Corp, Greensboro, N.C.) and 2,2'-dihydroxy-5,5'-dibromo-diphenyl ether; p-nitrophenol, picric acid, xylenol, phenoxyethanol, chlorinated phenols such as parachlorometaxylenol, p-chloro-o-benzylphenol and -dichlorophenol, cresols such as p-chloro-m-cresol, pyrocatechol, resorcinol, 4-n-hexylresorcinol, pryogallol, phloroglucin, carvacrol, thymol, p-chlorothymol, o-phenylphenol, o-benzylphenol, phenol, 4-ethylphenol, 4-phenolsulfonic acids, hexachlorophene, tetrachlorophene, dichlorophene, 2,3-dihydroxy-5,5'-dichlorophenyl sulfide, 2,2'-dihydroxy-3,3',5,5'-tetrachlorodiphenyl sulfide, 2,2'-dihydroxy-3,3',5,5',6,6'-hexachlorodiphenyl sulfide and 3,3'-dibromo-5,5'-dichloro-2,2'-dihydroxydiphenylamine. Preferred is triclosan at a concentration of between about 0.1 and 2 percent and most preferably between about 0.3 and 1 percent. Other phenols may be comprised at concentrations of between about 0.3 and 2 percent, but preferably at concentrations equivalent in potency against S. aureus as between 0.3 and 1 percent triclosan.

Additional antimicrobial agents which may be incorporated into compositions of the invention include antifungal agents such as miconazole (preferably at a concentration of 1–2 percent), polymixin (preferably at a concentration of 0.3–1 percent), neomycin (preferably at a concentration of 0.1–0.5 percent), iodine compounds such as povidone iodine (preferably at a concentration of 1–10 percent), minocycline (preferably at a concentration of 0.3–1.0 percent), and metal salts such as silver sulfadiazine (preferably at a concentration of 1–2 percent).

Preferred non-limiting embodiments of the invention comprise octoxyglycerin together with a quaternary ammonium compound, such as, but not limited to, benzalkonium chloride ("BZK", which is particularly preferred), benzethonium chloride, other benzalkonium or benzethonium halides, including, but not limited to, benzalkonium or benzethonium bromide or fluoride, cetyl pyridinium chloride, dequalinium chloride, N-myristyl-N-methyl-morpholinium methyl sulfate, poly[N-[3-(dimethylammonio)propyl]-N'-[3-(ethyleneoxyethelene dimethylammoinio)propyl]urea dichloride], alpha-4-[1-tris (2-hydroxyethyl)ammonium chloride-2-butenyl]-omega-tris (2-hydroxyethyl)ammonium chloride, poly[oxyethylene (dimethyliminio)ethylene (dimethyliminio)-ethylene dichloride]. The concentrations of quaternary ammonium compound may be between about 0.01 and 0.3 percent; preferably the quaternary ammonium compound is benzalkonium chloride at a concentration between 0.05 and 0.2 percent, more preferably between 0.1 and 0.15 percent.

In certain non-limiting embodiments, compositions of the invention may further comprise one or more alcohol. Alcohols which may be used according to the invention include aliphatic alcohols, including, but not limited, most preferred ethanol or isopropyl alcohol, but also n-propyl alcohol, and mixtures thereof, at concentrations between about 20 and 85 percent and preferably 40 to 70 percent. Suitable alcohols also include fatty alcohols, such as cetyl alcohol, myristyl alcohol, stearyl alcohol, octyl alcohol, decyl alcohol, lauryl alcohol, and combinations thereof, at concentrations between about 0.5 and 5 percent. The present invention further provides for compositions comprising, as at least one alcoholic component, hexanol at a concentration of between three and ten percent and preferably about 5 percent.

The formulations of the invention may further comprise one or more of the following:

A zinc-containing compound such as a zinc salt, including but not limited to zinc gluconate, zinc oxide, zinc stearate, zinc salicylate, zinc carbonate, zinc oleate, zinc acetate, zinc peroxide, zinc phosphate, and zinc undecylenate. Zinc compounds are known to have anti-irritant activity (see, for example, U.S. Pat. No. 5,965,610 by Modak et al. and U.S. Pat. No. 5,985,918 by Modak et al., incorporated by reference herein). Preferred zinc compounds for use according to the invention are, for a disinfecting alcohol gel, zinc gluconate and zinc oxide, at concentrations between 0.1 and 1 percent, and preferably 0.8 percent zinc gluconate and 0.2 percent zinc oxide; for an antiseptic aqueous formulation, zinc gluconate and zinc stearate, at concentrations between 0.2 and 7 percent, and preferably 2.4 percent zinc gluconate and 3.8 percent zinc stearate.

An emollient, which may be, for example, an organic, a hydrocarbon-based or a fatty-ester based emollient. Suitable hydrocarbon-based emollients include petrolatum and mineral oils. Suitable fatty ester based emollients include methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$–$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter.

A humectant, such as, for example, glycerine, 1-2-propylene glycol, dipropylene glycol, polyethylene glycol, 1,3-butylene glycol, or 1,2,6-hexanetriol.

A thickening and/or gelling agent, such as, for example, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9–15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, hydroxypropylcellulose, hydroxypropyl guar, hydroxypropyl methylcellulose, isocetyl alcohol, isostearyl alcohol, karaya gum, kelp, lauryl alcohol, locust bean gum, magnesium aluminum silicate, magensium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminum polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentotnite, stearalkonium hectorite, stearyl alcohol, tallow alcohol, TEA-hydrochloride, tragacanth gum, tridecyl alcohol, tromethamine magnesium aluminum silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, behenyl alcohol, butadiene/acrylonitrile copolymer, C29–70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6–14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, phthalic anhydride/glycerine/glycidyl decanoate copolymer, phthalic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl alcohol, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof.

A neutralizing agent, which may be included, for example, to neutralize carboxyl groups present in one or more other component, such as carboxyl groups in a thickening agent. Suitable neutralizing agents include diisopropylamine and triethanolamine.

A surfactant, which may be an anionic surfactant, a cationic surfactant, an ampholytic surfactant, or a nonionic surfactant, such as, for example, nonionic surfactants such as polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. A preferred surfactant is lauroyl ethylenediamine triacetic acid sodium salt at a concentration between about 0.5–2.0%. Suitable concentrations of surfactant are between about 0.05 and 2 percent.

Water used in the formulations is preferably deionized water having a neutral pH.

Additional additives, including but not limited to a silicone fluid (such as dimethicone or cyclomethicone), dyes, fragrances, etc. Examples of additional additives include but are not limited to: pH adjusters, including basic pH adjusters such as ammonia, mono-, di- and tri- alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); vitamins such as vitamin A, vitamin E and vitamin C; polyamino acids and salts, such as ethylenediamine tetraacidic acid (EDTA), preservatives such as DMDM hydantoin, and sunscreens such as aminobenzoic acid, arobenzone, cinoxate, diioxybenzone, homosalate, menthyl anthranilate, octocrylene, octyl methoxycinnamate, octyl salicylate, oxybenzoate, padimate O, phenylbenzimidazole, sulfonic acid, sulisobenzone, titanium dioxide, trolamine salicylate and zinc oxide.

Specific, non-limiting embodiments of the invention include the following compositions, which may further comprise additional ingredients which do not substantially effect the antimicrobial properties of the composition. For the following formulations, the water indicated was added last to the other ingredients to brind the total volume to 100 percent.

1. An antiseptic alcohol gel comprising:

| | |
|---|---|
| zinc gluconate | 0.8 percent |
| zinc oxide | 0.2 percent |
| ethyl alcohol | 65.0 percent (volume/volume) |
| hydroxy methyl propyl cellulose (K100M) | 0.3 percent |
| Ucare JR 400 (polyquaternium-10) (Amerchol Corp.) | 0.15 percent |
| Incroquat Behenyl TMS (Croda, Inc.) | 1.0 percent |
| Polawax A-31 (Croda, Inc.) | 1.0 percent |
| stearyl alcohol - Crodacol(S70) (Croda, Inc.) | 1.0 percent |
| Cremerol HMG (Amerchol Corp.) | 1.0 percent |
| dimethicone | 0.5 percent (volume/volume) |
| Germall plus (ISP Sutton Laboratories) | 0.25 percent |
| propylene glycol | 1.5 percent (volume/volume) |
| glycerine | 1.0 percent (volume/volume) |
| water | 23.13 percent (volume/volume) |
| chlorhexidine digluconate | 0.05 percent |
| phenoxyethanol | 1.0 percent |
| BZK | 0.12 percent |
| Sensiva SC50 | 2 percent (volume/volume) | where the gel may be applied to and rubbed over the skin to achieve its antimicrobial effect.

2. An antiseptic alcohol gel comprising:

| | |
|---|---|
| water | 31.32 percent (volume/volume) |
| Ucare (Amerchol Corp.) | 0.08 percent |
| hydroxypropylmethylcellulose (K-100) (Dow Corning) | 0.15 percent |
| Polyox WSR 301 (polyethyleneoxide) (Dow Corning) | 0.03 percent |
| Incroquat (Croda, Inc.) | 0.4 percent |
| Polawax A-31 (Croda, Inc.) | 0.4 percent |
| polyethylene glycol | 0.25 percent |
| ethanol | 63.5 percent (volume/volume) |
| Glucam E-20 (Amerchol Corp.) | 0.4 percent |
| Silicone 225 (Dow Corning) | 0.1 percent (volume/volume) |
| Sensiva SC50 | 2.0 percent (volume/volume) |
| phenoxyethanol | 1.0 percent |
| chlorhexidine digluconate | 0.05 percent |
| BZK | 0.12 percent |
| Germall Plus (Sutton Laboratories) | 0.2 percent |

3. An antiseptic aqueous formulation comprising:

| | |
|---|---|
| zinc gluconate | 2.4 percent |
| zinc stearate | 3.8 percent |
| hydroxy methyl propyl cellulose (K100M) | 0.5 percent |
| Kytamer PC (Chitisan) (Amerchol Corp.) | 0.15 percent |
| Ucare JR 400 (Amerchol Corp.) | 0.1 percent |
| Incroquat behenyl TMS (Croda, Inc.) | 1.0 percent |
| Crodamol NM (Croda, Inc.) | 1.6 percent |
| Acetulan (Amerchol Corp.) | 2.0 percent |
| Cremerol HMG (Amerchol Corp.) | 1.0 percent |
| stearyl alcohol | 2.0 percent |
| allantoin | 0.25 percent |
| Germall Plus (ISP Sutton Laboratories) | 0.3 percent |
| dimethicone | 1.0 percent (volume/volume) |
| water | 81.48 percent (volume/volume) |
| PHMB | 0.3 percent |
| phenoxyethanol | 1.0 percent |
| BZK | 0.12 percent |
| Sensiva SC50 | 2 percent (volume/volume) |

4. An antimicrobial scrub gel comprising:

| | |
|---|---|
| water | 30.5 percent |
| Ucare (Amerchol Corp.) | 0.1 percent |
| hydroxy propyl methyl cellulose (K100) (Dow Corning) | 0.2 percent |
| Polyox WSR 301 (polyethyleneoxide) (Dow Corning) | 0.1 percent |
| Incroquat (Croda, Inc.) | 0.4 percent |
| Polawax A-31 (Croda, Inc.) | 0.4 percent |
| propylene glycol | 1.0 percent |
| ethanol | 63.5 percent (volume/volume) |
| Glucam E-20 (Amerchol Corp.) | 0.4 percent |

-continued

| | |
|---|---|
| Masil SF 19 CG surfactant | 1.0 percent |
| phenoxyethanol | 1.0 percent |
| Sensiva SC50 | 1.0 percent (volume/volume) |
| chlorhexidine digluconate | 0.05 percent |
| BZK | 0.12 percent |
| Germall Plus | 0.2 percent |
| (Sutton Laboratories) | |

5. An antimicrobial scrub gel, for example for pre-operative skin disinfection, comprising:

| | |
|---|---|
| ethanol | 35 percent (volume/volume) |
| isopropanol | 35 percent (volume/volume) |
| zinc gluconate | 0.5 percent |
| zinc oxide | 0.2 percent |
| hydroxy methyl propyl cellulose (K100M) | 0.3 percent |
| Germall Plus (ISP Sutton Laboratories) | 0.25 percent |
| hexanol | 5.0 percent (volume/volume) |
| PXE | 1.0 percent |
| Sensiva | 1.5 percent (volume/volume) |
| chlorhexidine digluconate | 0.05 percent |
| with water added to 100 percent (approximately 21.2 milliliters/100 ml solution). | | with water added to a 100 percent (approximately 21.1 milliliters/100 ml solution).

6. Another antimicrobial scrub gel, for example for pre-operative skin disinfection, comprising:

| | |
|---|---|
| water | 23.28 percent (volume/volume) |
| Polyox WSR 205 | 0.2 percent |
| U-care JR 400 | 0.2 percent |
| ethanol (95%) | 65 percent (volume/volume) |
| propylene glycol | 3 percent |
| Sensiva SC50 | 2 percent (volume/volume) |
| BZK | 0.12 percent |
| phenoxyethanol | 1.0 percent |
| povidone iodine | 5.0 percent |
| Germall Plus | 0.2 percent |

7. An antimicrobial soap comprising:

| | |
|---|---|
| water | 51.2 percent (volume/volume) |
| Ucare (Amerchol Corp.) | 0.1 percent |
| hydroxy propyl methyl cellulose (K-100) (Dow Corning) | 0.2 percent |
| Polyox WSR 301 (polyethyleneoxide) | 0.03 percent |
| ethanol | 40 percent (volume/volume) |
| Pluronic F-87 (BASF) | 2.0 percent |
| Masil SF 19 CG surfactant | 1.0 percent |
| Cocamidopropyl betaine (Witco Corp.) | 2.0 percent |
| propylene glycol | 1.0 percent |
| phenoxyethanol | 1.0 percent |
| chlorhexidine digluconate | 0.05 percent |
| BZK | 0.12 percent |
| Sensiva SC50 | 0.5 percent (volume/volume) |
| Germall Plus (Sutton Laboratories) | 0.2 percent |

8. An antifungal cream comprising miconazole (1–2 percent), chlorhexidine digluconate (0.05–0.2 percent), and Sensiva SC50(1–3 percent) in a hydrophillic cream base.

9. A topical antiseptic ointment for wound care comprising polymixin (0.3–1%), neomycin (0.1–0.5 percent), chlorhexidine digluconate (0.05–0.2 percent), and Sensiva SC50(1–3 percent) in a hydrophillic base.

10. A topical antiseptic ointment for burn wound care comprising silver sulfadiazine (1–2 percent), chlorhexidine digluconate (0.05–0.2 percent) and Sensiva SC50 (1–3 percent) in a hydrophillic base.

5. EXAMPLES

Example 1

Sensiva+BZK

Sensiva SC50 and/or benzalkonium chloride ("BZK") were added, in various concentrations, to the following alcohol gel base:

| | |
|---|---|
| ethyl alcohol | 65 percent (volume/volume) |
| hydroxy methyl propyl cellulose (K100M) | 0.3 percent |
| hydroxy propyl cellulose (HF) | 0.1 percent (volume/volume) |
| Glucam P20 | 1.0 percent (volume/volume) |
| Glucam P20 distearate | 1.5 percent (volume/volume) |
| Ucare JR 400 (polyquaternium-10) | 0.15 percent |
| silicone (DC 1403) | 1.5 percent (volume/volume) |
| Germall Plus | 0.25 percent | to which water was added, after the incorporation of other additives, to bring the total volume to 100 percent (typically requiring approximately 20–30 percent (volume/volume)). The amount of Sensiva, throughout the example section, is a volume/volume percentage.

Antimicrobial activity was evaluated using the following assay. 1 milliliter of $10^8$ colony forming units ("cfus") of test organism per milliliter was added to 1 milliliter of bovine adult serum in a sterile culture tube and mixed. 1 milliliter of the test gel was added to each tube, and was vortexed to mix. After 15 seconds, three 0.5 ml aliquots were removed and further diluted 1:1000 with LTSB (lecithin-containing trypticase soy broth) drug inactivating medium, and, of the resulting liquid, 0.5 milliliters were plated on each trypticase soy agar ("TSA") plate. The resulting plates were incubated at 37° C. for 24 hours and the colony count per tube was determined.

The foregoing method was used to determine the antimicrobial activities of formulations of the above alcohol gel base comprising either Sensiva SC50, BZK or combinations of Sensiva SC50 and BZK. The results for Sensiva SC50 used alone are shown in Table 1, and the results for Sensiva SC50, BZK and Sensiva SC50/BZK combinations are shown in Table 2.

TABLE 1

| | % Sensiva | | | | | |
|---|---|---|---|---|---|---|
| | 0 | 0.5 | 1.0 | 2.0 | 3.0 | 5.0 |
| S. aureus (cfu/tube) | $1 \times 10^8$ | $1 \times 10^7$ | $4 \times 10^7$ | $3 \times 10^6$ | $1 \times 10^6$ | $1 \times 10^6$ |
| fold-reduction* | — | 2.5 | 9 | 33 | 100 | 100 |

*relative to control

TABLE 2

| | % Sensiva | | | | | | | | | |
|---|---|---|---|---|---|---|---|---|---|---|
| | 0 | 1.0 | 2.0 | 0 | 0 | 0 | 1.0 | 1.0 | 2.0 | 2.0 |
| | % BZK | | | | | | | | | |
| | 0 | 0 | 0 | 0.12 | 0.19 | 0.5 | 0.12 | 0.19 | 0.12 | 0.19 |
| S. aureus (cfu/tube) | $1 \times 10^8$ | $4 \times 10^7$ | $3 \times 10^6$ | $1.6 \times 10^7$ | $2 \times 10^7$ | $3.7 \times 10^6$ | $8 \times 10^5$ | $2 \times 10^4$ | $8 \times 10^3$ | $3.0 \times 10^3$ |
| Log 10 cfu reduction relative to control | — | 1 | 1.5 | 0.8 | 0.7 | 1.4 | 2.1 | 3.7 | 4.1 | 4.5 |
| Increase in log 10 beyond additive effect | NA | NA | NA | NA | NA | NA | 0.3 | 2 | 1.8 | 2.3 |
| fold reduction relative to control | — | 10 | 33 | 6.25 | 5 | 27 | 125 | $5 \times 10^3$ | $1.25 \times 10^4$ | $3.3 \times 10^4$ |

Tables 1 and 2 show that no significant antimicrobial activity against S. aureus was obtained with 2–5 percent Sensiva; the antimicrobial activity was not significantly different between 2, 3 and 5 percent of Sensiva. Similarly, 0.12 and 0.19 percent BZK exhibited minimal or no antimicrobial activity (Table 2). However, combinations of 1–2 percent Sensiva SC50 and 0.12–0.19 percent BZK showed 5000–33000 fold reduction in colony forming units compared to control values (Table 2).

Example 2

Sensiva+Chlorhexidine Digluconate

Assays using the same gel base and protocol as set forth in Example 1 to test activities of Sensiva, chlorhexidine digluconate ("CHG"), and combinations thereof gave the following results, shown in Table 3.

Thus, Sensiva SC50 (1–2 percent) and CHG (0.05–0.5 percent) used individually showed 9–35 fold reduction in colony counts as compared to control, whereas a combination of 1–2 percent Sensiva with 0.05–0.5 percent CHG showed 800–100,000 fold reduction. Thus, the combination of Sensiva and CHG appears to be synergistic. When benzalkonium chloride was added to formulation, the antimicrobial activity was improved still further, as shown in the following example section.

Example 3

Sensiva+Chlorhexidine Digluconate+BZK

Assays using the same gel base and protocol as set forth in Example 1 to test activities of combinations of Sensiva, chlorhexidine digluconate ("CHG") and BZK gave the following results, shown in Table 4.

TABLE 3

| | % Sensiva | | | | | | | | | |
|---|---|---|---|---|---|---|---|---|---|---|
| | 0 | 0 | 0 | 0 | 1.0 | 1.0 | 1.0 | 2.0 | 2.0 | 2.0 |
| | % CHG | | | | | | | | | |
| | 0 | 0.05 | 0.25 | 0.5 | 0.05 | 0.25 | 0.5 | 0.05 | 0.25 | 0.5 |
| S. aureus (cfu/tube) | $1 \times 10^8$ | $1.1 \times 10^7$ | $8 \times 10^6$ | $4.2 \times 10^6$ | $1.2 \times 10^5$ | $6 \times 10^4$ | $8 \times 10^3$ | $8 \times 10^3$ | $5 \times 10^3$ | $1 \times 10^3$ |
| Log 10 cfu reduction relative to control | — | 1.0 | 1.1 | 1.4 | 2.9 | 3.1 | 4.1 | 4.1 | 4.3 | 4.3 |
| Increase in log 10 beyond additive effect | NA | NA | NA | NA | 0.4 | 1.1 | 1.7 | 1.6 | 1.7 | 2.4 |
| fold reduction relative to control | — | 9 | 12.5 | 23.8 | 833 | 1666 | 12500 | 12500 | 20000 | $1 \times 10^5$ |

TABLE 4

| % Sensiva | 0 | 0 | 1.0 | 2.0 |
|---|---|---|---|---|
| % BZK | 0 | 0.12 | 0.12 | 0.12 |
| % CHG | 0 | 0.05 | 0.05 | 0.05 |
| Growth (cfu/ml) | $1 \times 10^8$ | $1.2 \times 10^7$ | $4 \times 10^4$ | 0 |
| Log 10 cfu reduction relative to control | 0 | 1.0 | 4.0 | 8.0 |
| Increase in log 10 beyond additive effect | NA | NA | 2.1 | 5.1 |
| fold reduction relative to control | — | 8.3 | 2500 | $10^8$ |

NA = not applicable

Example 4

Combinations of Sensiva and Other Antimicrobials

Since Sensiva does not exhibit potent microbicidal activity even at concentrations of between 3 and 5 percent, it is surprising that this compound exhibits synergism with chlorhexidine digluconate and BZK. Octoxyglycerin (Sensiva) has been reported to have the property of deeper penetration into the upper layers of the epidermis. Without being bound by any particular theory, the mechanism of synergistic action may be explained as follows. When a bacterium is exposed to Sensiva and a second antimicrobial agent, Sensiva may penetrate through the bacterial cell wall and thereby compromise the bacterial transport system. This may result in increased uptake of the second antimicrobial agent. This mechanism would indicate that Sensiva would promote the antimicrobial effects of a diverse array of compounds, including quaternary ammonium compounds, biguanides, chlorinated phenols, metal salts, antifungal azoles, etc.

Accordingly, the antimicrobial activity of various combinations of Sensiva and other antimicrobials was tested, using concentrations that fall within the recommended usage range for topical formulations. The following agents were tested. Benzalkonium chloride (BZK) and benzethonium chloride (BZT) were tested as representative of the class of quaternary ammonium compounds. Chlorhexidine digluconate (CHG) and polyhexamethylene biguanide (PHMB) were tested as representative of the class of biguanides. Parachlorometaxylenol (PCMX) and triclosan (TC) were tested as representative of the class of chlorinated phenols. Povidone iodine (PVI) was tested as representative of the class of iodine compounds. Silver sulfadiazine (AgSD) was tested as representative of the class of metal salts. Neomycin and miconazole were tested as representative of the class of antibiotics. The alcohol gel base and protocol set forth in Example 1 were used to produce the data set forth in Table 5.

Similar protocols were then used to test the antibacterial activity of Sensiva combined with chorhexidine digluconate and another antimicrobial agent. The results are shown in Table 6.

TABLE 5

| % Antimicrobial | % Sensiva | Growth (CFU/ml) | fold reduction* |
|---|---|---|---|
| 0 Control | 0 | $1 \times 10^8$ | — |
| 0 | 2.0 | $3 \times 10^6$ | 33 |
| BZK | | | |
| 0.12 | 0 | $1.6 \times 10^7$ | 6.25 |
| 0.12 | 2.0 | $8.0 \times 10^3$ | 12,500 |
| BZT | | | |
| 0.12 | 0 | $1.0 \times 10^7$ | 10 |
| 0.12 | 2.0 | $5.0 \times 10^3$ | 20,000 |
| CHG | | | |
| 0.05 | 0 | $1.1 \times 10^7$ | 9 |
| 0.05 | 2.0 | $8.0 \times 10^3$ | 12,500 |
| PHMB | | | |
| 0.3 | 0 | $3.0 \times 10^6$ | 33 |
| 0.3 | 2.0 | $4.0 \times 10^3$ | 25,000 |
| TC | | | |
| 0.3 | 0 | $1.0 \times 10^8$ | 0 |
| 0.3 | 2.0 | $2.2 \times 10^5$ | 450 |
| PCMX | | | |
| 0.3 | 0 | $1.0 \times 10^8$ | 0 |
| 0.3 | 2.0 | $6.2 \times 10^4$ | 1612 |
| AgSD | | | |
| 1.0 | 0 | $1.0 \times 10^8$ | 0 |
| 1.0 | 2.0 | $3.0 \times 10^5$ | 330 |
| PVI | | | |
| 1.0 | 0 | $2.0 \times 10^7$ | 5 |
| 1.0 | 2.0 | $3.0 \times 10^4$ | 3,333 |
| Neomycin | | | |
| 0.3 | 0 | $2.3 \times 10^7$ | 4.3 |
| 0.3 | 2.0 | $1.0 \times 10^3$ | 100,000 |
| Miconazole | | | |
| 1.0 | 0 | $1.0 \times 10^8$ | 0 |
| 1.0 | 2.0 | $6.0 \times 10^4$ | 1666 |

*relative to control

TABLE 6

| % Antimicrobial | % Sensiva | % CHG | Growth (CFU/ML) | Fold Reduction Compared to Control |
|---|---|---|---|---|
| 0 | 0 | 0 | $1.0 \times 10^8$ | — |
| 0 | 2.0 | 0 | $3.0 \times 10^6$ | 33 |
| 0 | 2.0 | 0.05 | $8.0 \times 10^3$ | 12,500 |
| BZK | | | | |
| 0.12 | 0 | 0.05 | $1.2 \times 10^7$ | 8.3 |
| 0.12 | 2.0 | 0.05 | 0 | $10^8$ |
| TC | | | | |
| 0.3 | 0 | 0.05 | $9.0 \times 10^6$ | 11.1 |
| 0.3 | 2.0 | 0.05 | 0 | $10^8$ |
| PCMX | | | | |
| 0.3 | 0 | 0.05 | $7.0 \times 10^6$ | 14.2 |
| 0.3 | 2.0 | 0.05 | 0 | $10^8$ |
| AgSD | | | | |
| 1.0 | 0 | 0.05 | $1.0 \times 10^7$ | 10 |
| 1.0 | 2.0 | 0.05 | 0 | $10^8$ |
| PVI | | | | |
| 1.0 | 0 | 0.05 | $1.0 \times 10^7$ | 10 |
| 1.0 | 2.0 | 0.05 | 0 | $10^8$ |

TABLE 6-continued

| % Antimicrobial | % Sensiva | % CHG | Growth (CFU/ML) | Fold Reduction Compared to Control |
|---|---|---|---|---|
| Neomycin | | | | |
| 0.3 | 0 | 0.05 | $1.0 \times 10^6$ | 100 |
| 0.3 | 2.0 | 0.05 | 0 | $10^8$ |

The data shown in Table 5 indicate that Sensiva, at a concentration of 2.0 percent, produced a 33-fold reduction in bacterial colony formation, and the antibacterial activity of the other antimicrobials tested, used alone, was less than or equal to 33-fold. Combination of these antimicrobials with Sensiva greatly resulted in an antibacterial activity greater than what would have been expected, based on the inhibitory activity of either agent used separately. The extent of this enhancement varied among antimicrobials; for example, the activity of quaternary ammonium compounds, used in combination with Sensiva, was observed to be 12,500 and 20,000-fold greater than control. The biguanides chlorhexidine digluconate and parahexamethylenebiguanide, in combination with Sensiva, produced an antimicrobial activity 12,500 and 25,000-fold greater, respectively, than control. Neomycin, in combination with Sensiva, exhibited an antimibrobial activity 100,000 greater than control. Thus, Sensiva has been demonstrated to enhance the antimicrobial effects of a wide variety of agents. The data shown in Table 6 further show that combinations of Sensiva and chlorhexidine digluconate with various antimicrobials exhibit a further enhancement in activity.

Example 5

Additional Data

Assays using the same gel base and protocol as set forth in Example 1 to test activities of combinations of Sensiva and other antimicrobials gave the following results, shown in Table 7.

TABLE 7

| Agent(s) | Concentrations | Growth (cfu/tube) |
|---|---|---|
| control (without gel base) | — | $2.5–4.2 \times 10^8$ |
| Sensiva | 0.5 | $4.0 \times 10^7$ |
| Sensiva | 1.0 | $1.0 \times 10^7$ |
| BZK | 0.019 | $8.0 \times 10^7$ |
| BZK + Sensiva | 0.019 1.0 | $2.0 \times 10^7$ |
| BZK + Sensiva | 0.019 2.0 | $1.2 \times 10^7$ |
| BZK | 0.12 | $1.6 \times 10^7$ |
| BZK + Sensiva | 0.12 0.5 | $1.4 \times 10^7$ |
| BZK + Sensiva | 0.12 1.0 | $8.0 \times 10^5$ |
| CHG | 0.05 | $1.1 \times 10^7$ |
| CHG + Sensiva | 0.05 0.5 | $6.3 \times 10^6$ |
| CHG + Sensiva | 0.05 1.0 | $1.2 \times 10^5$ |
| PCMX | 0.15 | $3.5 \times 10^8$ |
| PCMX + Sensiva | 0.15 2.0 | $4.1 \times 10^5$ |
| TC + BZK | 0.3 0.12 | $1.0 \times 10^7$ |

TABLE 7-continued

| Agent(s) | Concentrations | Growth (cfu/tube) |
|---|---|---|
| TC + BZK + Sensiva | 0.3 0.12 2.0 | $4.0 \times 10^3$ |
| PCMX + BZK | 0.3 0.12 | $2.0 \times 10^6$ |
| PCMX + BZK + Sensiva | 0.3 0.12 2.0 | $1.0 \times 10^3$ |
| Miconazole + CHG | 1.0 0.05 | $1.0 \times 10^7$ |
| Miconazole + CHG + Sensiva | 1.0 0.05 2.0 | $1.0 \times 10^3$ |
| PVI + CHG | 1.0 0.05 | $1.0 \times 10^7$ |
| PVI + CHG + Sensiva | 1.0 0.05 2.0 | 0 |

Example 6

Combinations of Sensiva, BZK, and Other Agents

Again using the alcohol gel base and protocol described in Example 1, various combinations of Sensiva, the quaternary ammonium compound BZK, and other antimicrobials produced the results shown in Table 8.

TABLE 8

| Agent(s) | Concentration (%) | Growth (cfu/tube) |
|---|---|---|
| Control (no gel base) | — | $2.0 \times 10^8$ |
| Control (gel base) | — | $1.2 \times 10^8$ |
| PXE | 1.0 | $1.0 \times 10^8$ |
| PXE + Sensiva | 1.0 1.0 | $2.0 \times 10^7$ |
| PXE + Sensiva | 1.0 2.0 | $3.3 \times 10^5$ |
| BZK + CHG + Sensiva | 0.12 0.05 1.0 | $4.0 \times 10^4$ |
| BZK + CHG + Sensiva | 0.12 0.05 2.0 | 0 |
| BZK + CHG + Sensiva + PXE | 0.12 0.05 1.0 1.0 | 0 |
| BZK + PHMB + Sensiva | 0.12 0.3 1.0 | $8.0 \times 10^3$ |
| BZK + PHMB + Sensiva + PXE | 0.12 0.3 1.0 1.0 | 0 |

The above data demonstrates that the addition of the phenol derivative, phenoxyethanol, enhanced the antimicrobial activity of several combinations of Sensiva and other antimicrobials.

Example 7

Sustained Activity of Antimicrobial Preparations

Natural leather was cut into 2×2 cm pieces, washed, and sterilized. For each test group 4 pieces were used. Equal amounts (0.25 ml) of various test formulations were applied uniformly on the surface of each piece, and then allowed to dry for 3 hours. Then 10 microliters of a *Staphylococcus aureus* culture ($10^7$ CFU/ml) was spread uniformly on the surface of the treated leather patches. After 1 minute, the inoculated side of the leather was rinsed with 10 ml of drug inactivating medium (LTSB), of which a 0.5 ml aliquot was plated on the surface of a D/E (drug inactivating) plate. Plates prepared in this manner were incubated for 24 hours at 37° C. and bacterial colonies were counted. The results, which demonstrate sustained antimicrobial activity of the Sensiva formulations, are shown in Table 9.

TABLE 9

| Group | *Staphylococcus aureus* CFU/patch |
|---|---|
| 0.12% BZK + 0.5% PXE + 0.05% CHG + 1.0% Sensiva | 30 |
| 0.12% BZK + 0.5% PXE + 0.3% PHMB + 1.0% Sensiva | 20 |
| Prevacare | $1.3 \times 10^4$ |
| Gel Base (control) | $1.1 \times 10^4$ |
| Control | $1.2 \times 10^5$ |

Example 8

Aqueous Sensiva Formulation

For the experiments to be described below, the following aqueous base was used:

| | |
|---|---|
| hydroxy methyl propyl cellulose (K100M) | 0.5 percent |
| Kytamer PC (Chitisan) | 0.15 percent |
| Ucare JR-400 | 0.1 percent |
| Incroquat Behenyl TMS | 1.0 percent |
| Crodamol NM | 1.6 percent |
| Acetulan | 2.0 percent |
| Cremerol HMG | 1.0 percent |
| stearyl alcohol | 2.0 percent |
| allantoin | 0.25 percent |
| Germall Plus | 0.3 percent |
| dimethicone | 1.0 percent (volume/volume) | and then water was added to bring to volume up to 100 percent. Various antimicrobials were added to this aqueous base, and then tested according to the protocol set forth in Example 1. The results are shown in Table 10.

TABLE 10

| Group | *Staphylococcus aureus* (CFU/tube) |
|---|---|
| aqueous base (control) | $5.0 \times 10^8$ |
| 0.12% BZK | $2.0 \times 10^8$ |
| 1.0% PXE | $1.0 \times 10^8$ |
| 0.5% PXE | $3.4 \times 10^8$ |
| 1.0% Sensiva | $5.0 \times 10^8$ |
| 0.05% CHG | $2.5 \times 10^8$ |
| 0.3% PHMB | $1.0 \times 10^7$ |
| 1% PXE + 1% Sensiva | $1.0 \times 10^8$ |
| 0.05% CHG + 1% Sensiva | $5.0 \times 10^6$ |
| 0.05% CHG + 1% PXE | $1.0 \times 10^8$ |
| 0.12% BZK + 1% Sensiva | $2.5 \times 10^6$ |
| 0.12% BZK + 1% PXE | $1.2 \times 10^7$ |
| 0.12% BZK + 1% PXB + 1% Sensiva | $4.0 \times 10^4$ |
| 0.12% BZK + 0.5% PXE + 0.05% CHG | $2.0 \times 10^5$ |
| 0.12% BZK + 0.5% PXE + 0.05% CHG + 0.3% PHMB | $2.7 \times 10^4$ |
| 0.12% BZK + 0.5% PXE + 0.05% CHG + 1% Sensiva | 0 |

TABLE 10-continued

| Group | *Staphylococcus aureus* (CFU/tube) |
|---|---|
| 0.12% BZK + 0.5% PXE + 0.3% PHMB + 1% Sensiva | 0 |
| 0.12% BZK + 0.5% PXE + 0.05% CHG + 0.3% PHMB + 1% Sensiva | 0 |
| negative control (no base/no agent) | $8.0 \times 10^8$ |

The foregoing experiments indicate that the potentiation of the antimicrobial activity of agents by Sensiva occurs in aqueous solution, in addition to the results observed using alcoholic gels. A combination of BZK, biguanide (CHG or PHMB), PXE and Sensiva achieved complete kill of test bacteria within 15 seconds.

Example 9

Sustained Activity of Aqueous Formulations

Various combinations of antimicrobials were incorporated in an aqueous base, as set forth in Example 8, and then tested for sustained activity on leather patches using the protocol set forth in Example 7. The results, which demonstrate enhanced sustained activity in the presence of Sensiva, are shown in Table 11.

TABLE 11

| Group | *Staphylococcus aureus* (CFU/patch) |
|---|---|
| 0.12% BZK + 0.5% PXE + 0.05% CHG + 0.3% PHMB | $2.0 \times 10^4$ |
| 0.12% BZK + 0.5% PXE + 0.05% CHG + 0.3% PHMB + 1% Sensiva | 0 |
| Aqueous Base (control) | $5.0 \times 10^5$ |
| Negative Control (no agent/no base) | $5.4 \times 10^5$ |

Example 10

Alcohol Gels Containing Sensiva and Zinc Anti-Irritants

In individuals whose skin is sensitive to alcohol or antiseptics, the use of antimicrobial alcoholic gels can be irritating, and may cause dermatitis. It has been found that certain zinc salts, selected from the group of zinc gluconate, zinc oxide and zinc stearate, can provide an anti-irritant effect (see U.S. Pat. No. 5,965,610 by Modak et al., issued Oct. 12, 1999 and U.S. Pat. No. 5,985,918 by Modak et al., issued Nov. 16, 1999). In alcohol gel formulations containing Sensiva, zinc compounds were added in irritation-preventing quantities and their antimicrobial effectiveness was tested. The formulation was as follows:

| | |
|---|---|
| zinc gluconate | 2.0 percent |
| ethanol | 63.5 percent (volume/volume) |
| Kytamer PC (Chitisan) | 0.1 percent |
| Ucare JR 400 (polyquaternium 10) | 0.08 percent |
| Germall Plus | 0.3 percent |
| Crodamol MM | 0.9 percent |
| Acetulan | 0.5 percent |

-continued

| | |
|---|---|
| Cremerol HMG | 1.0 percent |
| Incroquat | 1.5 percent |
| Polawax A-31 | 2.0 percent |
| hydroxy methyl propyl cellulose (K100M) | 0.4 percent |
| zinc stearate | 3.5 percent |
| allantoin | 0.2 percent |
| dimethicone | 0.5 percent (volume/volume) |
| propylene glycol | 1.5 percent (volume/volume) |
| glycerin | 1.0 percent (volume/volume) |
| Sensiva | 1.5 percent (volume/volume) |
| PXE | 1.0 percent |
| BZK | 0.12 percent |
| PHMB | 0.3 percent | and water was added to 100% (approx. 18 ml/100 ml formulation). The resulting formulation is referred to as a "cream".

To test for rapid antimicrobial activity, 0.8 ml of the above cream formulation was mixed with 0.1 ml of $10^9$/ml CFU of test organisms and 0.1 ml bovine adult serum. After 15 seconds, this mixture was diluted 1000-fold with LTSB drug-inactivating media and 0.5 ml of the resulting solution was subcultured on a TSA plate. The resulting plates were incubated for 24 hours at 37° C. and bacterial counts per tube were determined. To test for sustained antimicrobial activity, the method set forth in Example 7, using leather patches, was employed. The results of testing for rapid and sustained antimicrobial activities are shown in Table 12.

TABLE 12

| Formulation | Rapid Activity (CFU/tube) | Sustained Activity (CFU/patch) |
|---|---|---|
| Zn Gluconate 2% + Zn Stearate 3.5% + Sensiva 1.5% + PXE 1% + BZK 0.12% + PHMB 0.3% -containing cream* | 0 | 40 |
| Prevacare | 0 | $9.2 \times 10^3$ |
| Cream Without Antimicrobials** | $2.8 \times 10^5$ | $8.6 \times 10^3$ |
| Control | $6.5 \times 10^8$ | $2.3 \times 10^5$ |

*as comprised in the formulation set forth above in this example section.
**the formulation set forth above, omitting Sensiva, PXE, BZK and PHMB Example 11

Antiseptic Alcohol Gel Formulation Containing Zinc Salts

The following gel formulation has only a small amount of zinc salts. It was tested for rapid antimicrobial activity against *Staphylococcus aureus, Pseudomonas aeruginosa,* and *Escherichia coli* using the protocol set forth in Example 10. The results, which indicate that the formulation has activity against gram positive (*Staphylococcus aureus*) as well as gram negative (*Pseudomonas aeruginosa* and *Escherichia coli*) are shown in Table 13.

| | |
|---|---|
| ethyl alcohol | 63.5 percent (volume/volume) |
| zinc gluconate | 0.8 percent |
| zinc oxide | 0.25 percent |
| hydroxy methyl propyl cellulose (K100M) | 0.4 percent |

-continued

| | |
|---|---|
| Glucam P20 | 1.0 percent (volume/volume) |
| Glucam P20 distearate | 1.5 percent (volume/volume) |
| Ucare JR400 | 0.15 percent |
| silicone (DC 1403) | 1.5 percent (volume/volume) |
| Germall Plus | 0.25 percent |
| PHMB | 0.3 percent |
| PXE | 1.5 percent |
| BZK | 0.12 percent |
| Sensiva | 1.5 percent | with water added to 100 percent (approx. 27.2 ml/100 ml).

TABLE 13

| Formulation | S. aureus CFU/tube | P. aeruginosa CFU/tube | E. coli CFU/tube |
|---|---|---|---|
| Zn gluconate 0.8% + Zn oxide 0.2% + PHMB 0.3% + PXE 1.5% + BZK 0.12% + Sensiva 1.5% gel* | 0 | $1.0 \times 10^3$ | 0 |
| Prevacare | 0 | ND | ND |
| Alcohol Gel Without Antimicrobials** | $3.2 \times 10^5$ | $5.0 \times 10^7$ | $1.0 \times 10^7$ |
| Control | $8.0 \times 10^8$ | $5.0 \times 10^8$ | $6.5 \times 10^8$ |

*gel formulation set forth above in this example section.
**gel formulation set forth above, lacking PHMB, PXE, BZK and Sensiva.

Example 12

Foaming Antimicrobial Gel

The following alcoholic foam formulation was prepared and tested for rapid antimicrobial activity according to the method set forth in Example 10, using *Staphylococcus aureus* as the test organism. The results are shown in Table 14. If more foaming is desired, a surfactant, such as lauroyl ethylenediamine triacetic acid sodium salt (0.5–2.0%) may be added to the following formulation.

| | |
|---|---|
| zinc gluconate | 0.25 percent |
| zinc acetate | 0.25 percent |
| ethanol | 65.0 percent (volume/volume) |
| Polyquaternium 22 | 2.0 percent |
| Pluronic Gel (F-87) | 0.075 percent (volume/volume) |
| BZK | 0.12 percent |
| CHG | 0.05% |
| PXE | 1.0 percent |
| Sensiva | 1.0 percent (volume/volume) | with water added to 100 percent (approx. 30.25 ml/100 ml).

TABLE 14

| Formulation | S. aureus CFU/tube |
|---|---|
| BZK 0.12% + CHG 0.05% + PXE 1.0% + Sensiva 1.0% foam (supra) | 0 |
| Above Foam Without BZK, CHG, PXE or Sensiva | $2.0 \times 10^5$ |
| Control | $3.9 \times 10^8$ |

Various publications are cited herein, the contents of which are hereby incorporated herein in their entireties by reference.

We claim:
1. An antimicrobial composition comprising synergistic effective amounts of octoxyglycerin, a quaternary ammo- nium compound, and an antimicrobial agent selected from the group consisting of biguanide compound, triclosan, phenoxyethanol, an iodine compound and parachlorometaxylenol.

2. The composition of claim 1 wherein the concentration of octoxyglycerin is between 1 and 5 percent (volume/volume).

3. The composition of claim 1 wherein the concentration of quaternary ammonium compound is between 0.01 and 0.3 percent.

4. The composition of claim 2 wherein the concentration of quaternary ammonium compound is between 0.01 and 0.3 percent.

5. The composition of claim 1 or 2 wherein the antimicrobial agent is a biguanide compound at a concentration of between 0.5 and 4 percent.

6. The composition of claim 5 wherein the biguanide compound is a chlorhexidine compound.

7. The composition of claim 3 or 4 wherein the antimicrobial agent is a biguanide compound at a concentration of between 0.5 and 4 percent.

8. The composition of claim 7 wherein the biguanide compound is a chlorhexidine compound.

9. The composition of claim 1 wherein the antimicrobial agent is triclosan at a concentration of between 0.1 and 2 percent.

10. The composition of claim 2 wherein the antimicrobial agent is triclosan at a concentration of between 0.1 and 2 percent.

11. The composition of claim 3 wherein the antimicrobial agent is triclosan at a concentration of between 0.1 and 2 percent.

12. The composition of claim 4 wherein the antimicrobial agent is triclosan at a concentration of between 0.3 and 2 percent.

13. The composition of claim 1 wherein the antimicrobial agent is phenoxyethanol at a concentration of between 0.3 and 2 percent.

14. The composition of claim 2 wherein the antimicrobial agent is phenoxyethanol at a concentration of between 0.3 and 2 percent.

15. The composition of claim 3 wherein the antimicrobial agent is phenoxyethanol at a concentration of between 0.3 and 2 percent.

16. The composition of claim 4 wherein the antimicrobial agent is phenoxyethanol at a concentration of between 0.3 and 2 percent.

17. The composition of claim 1 wherein the antimicrobial agent is parachlorometaxylenol at a concentration of between 0.3 and 2 percent.

18. The composition of claim 2 wherein the antimicrobial agent is parachlorometaxylenol at a concentration of between 0.3 and 2 percent.

19. The composition of claim 3 wherein the antimicrobial agent is parachlorometaxylenol at a concentration of between 0.3 and 2 percent.

20. The composition of claim 4 wherein the antimicrobial agent is parachlorometaxylenol at a concentration of between 0.3 and 2 percent.

21. The antimicrobial composition of claim 1 which further comprises between 20 and 85 percent (volume/volume) of ethanol.

22. The antimicrobial composition of claim 1 which further comprises between 20 and 85 percent (volume/volume) of isopropanol.

23. The antimicrobial composition of claim 1, 2 or 3 which further comprises between 3 and 10 percent (volume/volume) hexanol.

24. The antimicrobial composition of claim 1 which further comprises between 0.2 and 7 percent of a zinc compound selected from the group consisting of zinc gluconate, zinc oxide, zinc acetate, zinc stearate and zinc salicylate.

25. An antimicrobial composition comprising synergistic effective amounts of between 1 and 5 percent (volume/volume) octoxyglycerin, between 0.05 and 0.2 percent of benzalkonium chloride, and between 0.5 and 4 percent of chlorhexidine digluconate.

26. The antimicrobial composition of claim 25 which further comprises between 20 and 85 percent (volume/volume) of ethanol.

27. The antimicrobial composition of claim 25 which further comprises between 20 and 85 percent (volume/volume) of isopropanol.

28. The antimicrobial composition of claim 25 which further comprises between 3 and 10 percent (volume/volume) hexanol.

29. The antimicrobial composition of claim 25 which further comprises between 0.2 and 7 percent of a zinc compound selected from the group consisting of zinc gluconate, zinc oxide, zinc stearate and zinc salicylate.

30. An antimicrobial composition comprising synergistic effective amounts of between 1 and 5 percent (volume/volume) octoxyglycerin, between 0.5 and 4 percent of a chlorhexidine compound, and between 1 and 2 percent of miconazole.

31. An antimicrobial composition comprising synergistic effective amounts of between 1 and 5 percent (volume/volume) octoxyglycerin, between 0.5 and 4 percent of a chlorhexidine compound, and between 0.3 and 1 percent polymixin.

32. An antimicrobial composition comprising synergistic effective amounts of between 1 and 5 percent (volume/volume) octoxyglycerin, between 0.5 and 4 percent of a chlorhexidine compound, and between 0.1 and 0.5 percent neomycin.

33. The composition of claim 32, further comprising between 0.3 and 1 percent polymixin.

34. An antimicrobial composition comprising synergistic effective amounts of between 1 and 5 percent (volume/volume) octoxyglycerin, between 0.5 and 4 percent of a chlorhexidine compound, and between 1 and 2 percent silver sulfadiazine.

35. An antimicrobial composition comprising synergistic effective amounts of between 1 and 5 percent (volume/volume) octoxyglycerin, between 0.5 and 4 percent of chlorhexidine digluconate, and between 1 and 2 percent of miconazole.

36. An antimicrobial composition comprising synergistic effective amounts of between 1 and 5 percent (volume/volume) octoxyglycerin, between 0.5 and 4 percent of chlorhexidine digluconate, and between 0.3 and 1 percent polymixin.

37. An antimicrobial composition comprising synergistic effective amounts of between 1 and 5 percent (volume/volume) octoxyglycerin, between 0.5 and 4 percent of chlorhexidine digluconate, and between 0.1 and 0.5 percent neomycin.

38. The composition of claim 37, further comprising between 0.3 and 1 percent polymixin.

39. An antimicrobial composition comprising synergistic effective amounts of between 1 and 5 percent (volume/volume) octoxyglycerin, between 0.5 and 4 percent of chlorhexidine digluconate, and between 1 and 2 percent silver sulfadiazine.

40. An antimicrobial composition comprising synergistic effective amounts of between 1 and 5 percent (volume/volume) octoxyglycerin, between 0.05 and 2 percent of chlorhexidine digluconate, between 0.3 and 2 percent of phenoxyethanol, between 0.01 and 0.3 percent of a quaternary ammonium compound, and between 20 and 85 percent of an alcohol elected from the group consisting of ethanol and isopropyl alcohol.

* * * * *